(12) United States Patent
Rizkalla et al.

(10) Patent No.: US 8,883,675 B2
(45) Date of Patent: Nov. 11, 2014

(54) METHOD FOR MAKING A HIGHLY SELECTIVE ETHYLENE OXIDE CATALYST

(75) Inventors: Nabil Rizkalla, Rivervale, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 111 days.

(21) Appl. No.: 13/109,668

(22) Filed: May 17, 2011

(65) Prior Publication Data

US 2011/0281724 A1 Nov. 17, 2011

Related U.S. Application Data

(60) Provisional application No. 61/345,464, filed on May 17, 2010.

(51) Int. Cl.

| | |
|---|---|
| *B01J 23/50* | (2006.01) |
| *B01J 23/58* | (2006.01) |
| *B01J 37/02* | (2006.01) |
| *B01J 37/08* | (2006.01) |
| *C07D 301/08* | (2006.01) |
| *B01J 23/66* | (2006.01) |
| *C07D 301/10* | (2006.01) |
| *B01J 23/68* | (2006.01) |
| *B01J 21/04* | (2006.01) |

(52) U.S. Cl.
CPC .............. *B01J 23/66* (2013.01); *B01J 37/0201* (2013.01); *B01J 37/08* (2013.01); *C07D 301/08* (2013.01); *C07D 301/10* (2013.01); *B01J 23/688* (2013.01); *B01J 21/04* (2013.01)
USPC .............................. 502/348; 502/347; 502/330

(58) Field of Classification Search
USPC .......................................... 502/347, 348, 330
See application file for complete search history.

(56) References Cited

U.S. PATENT DOCUMENTS

| | | | |
|---|---|---|---|
| 4,005,049 A * | 1/1977 | Fields ............................ | 502/330 |
| 4,761,394 A | 8/1988 | Lauritzen | |
| 4,766,105 A | 8/1988 | Lauritzen | |
| 4,820,675 A | 4/1989 | Lauritzen | |
| 4,874,879 A | 10/1989 | Lauritzen et al. | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,155,242 A | 10/1992 | Shankar et al. | |
| 5,187,140 A | 2/1993 | Thorsteinson et al. | |
| 5,407,888 A | 4/1995 | Herzog et al. | |
| 5,504,052 A | 4/1996 | Rizkalla et al. | |
| 5,545,603 A | 8/1996 | Kemp | |
| 5,646,087 A | 7/1997 | Rizkalla et al. | |
| 5,739,075 A | 4/1998 | Matusz | |
| 6,609,863 B1 | 8/2003 | Morioka et al. | |
| 6,626,212 B2 | 9/2003 | Morioka et al. | |
| 6,913,028 B2 | 7/2005 | Morioka et al. | |
| 7,102,022 B2 | 9/2006 | Evans et al. | |
| 7,485,597 B2 | 2/2009 | Lockemeyer et al. | |
| 7,553,980 B2 | 6/2009 | Rizkalla et al. | |
| 2006/0252639 A1 | 11/2006 | Pak et al. | |
| 2008/0039316 A1 | 2/2008 | Bhise et al. | |
| 2010/0191006 A1 * | 7/2010 | Guckel .......................... | 549/536 |

FOREIGN PATENT DOCUMENTS

CN        1168644 A        12/1997

OTHER PUBLICATIONS

International Search Report dated Jan. 18, 2012 received in a corresponding foreign application.
Chinese Office Action dated Aug. 12, 2014 and translation thereof received in a corresponding foreign application.

* cited by examiner

*Primary Examiner* — Anthony J Zimmer
(74) *Attorney, Agent, or Firm* — Scully, Scott, Murphy & Presser, P.C.

(57) ABSTRACT

A process for the preparation of a catalyst useful for the vapor phase production of ethylene oxide from ethylene and oxygen comprising providing a catalyst precursor comprising an inert support having a catalytically effective amount of a silver containing compound, a promoting amount of an alkali metal containing compound, and a promoting amount of a transition metal containing compound disposed thereon; calcining the catalyst precursor to convert the silver in the silver containing compound to metallic silver by heating the catalyst precursor to form a catalyst; and curing the catalyst in an inert gas atmosphere at temperatures of about 250° C. to about 600° C. for a period of about 1 hour to 200 hours.

9 Claims, No Drawings

METHOD FOR MAKING A HIGHLY SELECTIVE ETHYLENE OXIDE CATALYST

CROSS REFERENCE TO RELATED APPLICATION

This application claims benefit of U.S. Provisional Patent Application Ser. No. 61/345,464, filed May 17, 2010, the entire content and disclosure of which is incorporated herein by reference.

FIELD OF THE INVENTION

This invention relates to a process for the preparation of a catalyst useful for the vapor phase production of ethylene oxide from ethylene and oxygen.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Thèodore Lefort. Lefort used a solid silver catalyst with a gas phase feed that included ethylene and utilized air as a source of oxygen. In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. Almost 65% of ethylene oxide is hydrolyzed to MEG, which is a precursor for important polymers such as polyester fibers and polyethylene terephthalate. The second largest market for EO is in surface active agents, primarily non-ionic alkylphenol ethoxylates and detergent alcohol ethoxylates. Ethylene oxide itself can be polymerized to form polyethylene glycol or polyethylene oxide, which are useful as non-toxic, water-soluble polymers. Ethylene oxide gas kills bacteria, mold, and fungi, and can therefore is used to sterilize substances that would be damaged by sterilizing techniques such as pasteurization that rely on heat. Additionally, ethylene oxide is widely used to sterilize medical supplies such as bandages, sutures, and surgical implements. Monoethanolamine is produced by reacting ethylene oxide with aqueous ammonia; the reaction also produces diethanolamine and triethanolamine.

Given ethylene oxide's importance in industrial chemistry it is not surprising that a wide variety of catalysts have been formulated for the manufacture of ethylene oxide, each catalyst having its own unique characteristics. The "standard" ethylene oxide catalyst that has been in longest use contains primarily silver and Cs deposited on a low surface area carrier. The performance of this catalyst, which is often referred to as "high activity catalyst" is expected to be stable and with starting selectivity of 80-83%. This high activity catalyst does not require any special treatment in order to provide the expected performance. In the last twenty years, however, research has focused not on high activity catalysts, but on the so-called "high selectivity catalysts", which are also Ag-based epoxidation catalysts. Among the high selectivity catalysts are those which contain small amounts of rhenium and cesium and other "promoting" elements. At optimum conditions, this type of catalyst provides selectivity in excess of 83% and can reach in excess of 90%.

With respect to these Re-containing catalysts there has been considerable interest in determining the optimum start-up (also commonly referred to as "initiation" or "activation") conditions, since Re-containing catalysts require an initiation period to maximize selectivity. Among some of the earliest disclosures of initiation procedures for high selectivity catalysts are those in U.S. Pat. No. 4,874,879 to Lauritzen et al. and U.S. Pat. No. 5,155,242 to Shanker et al., which disclose start-up processes in which Re-containing catalysts are pre-chlorinated prior to the introduction of oxygen into the feed and the catalysts are allowed to "pre-soak" in the presence of the chloride at a temperature below that of the operating temperature. While some improvement in overall catalyst performance has been reported using these methods, the pre-soaking nonetheless was not sufficient to provide the optimum performance of the Re-containing catalyst. Additionally, in order to reduce the deleterious effects on catalyst performance caused by overchloriding during the pre-soak phase, occasionally it is necessary to conduct an additional chlorine removal step.

More recent techniques for initiation or conditioning procedures are disclosed in U.S. Pat. No. 7,485,597 to Lockemeyer et al. In particular, this disclosure provides a method for improving the selectivity of a supported highly selective epoxidation catalyst comprising Ag in a quantity of at most 0.17 g per $m^2$ surface area of the support. The improvement was achieved by contacting the catalyst with a feed including oxygen at a catalyst temperature above 250° C. for duration of up to, at most, 150 hours.

Another start-up process is disclosed in U.S. Pat. No. 7,102,022 to Lockemeyer et al. Specifically, the '022 patent discloses a method for the start-up of a process for the epoxidation of an olefin comprising an Ag-based highly selectivity epoxidation catalyst. The method disclosed in the '022 patent includes contacting a catalyst bed with a feed comprising oxygen. In this treatment, the temperature of the catalyst bed was above 260° C. for a period of time of, at most, 150 hours.

U.S. Pat. No. 7,553,980 discloses an "initiation" method for epoxidation of ethylene comprising: contacting a catalyst bed including a silver-based highly selective epoxidation with a feed gas composition, at a first temperature during an initiation period, including ethylene, oxygen, a moderator and carbon dioxide, said carbon dioxide is at first concentration of greater than about 6 vol. %; increasing the first temperature to a second temperature, adjusting the feed gas composition in order to maintain said desired concentration of ethylene oxide while achieving a desired catalyst work rate. At the end of the initiation period, the second temperature is lowered to a third temperature.

In a co-pending patent application "Method for Preparing an Epoxidation Catalyst", U.S. Ser. No. 13/109,657 filed on the same date as the present application, a two-step calcination is disclosed that eliminates the need for the catalyst "initiation" or conditioning period. The treatment includes first heating the catalyst precursor in an inert atmosphere and then the calcination continues in an oxygen-containing atmosphere at a temperature from about 350° C. to about 450° C. for a time period of up to about 5 minutes.

While the treatment methods for activating a Re-containing epoxidation catalyst disclosed in the aforementioned prior publications may provide some improvement in catalyst performance, they also have several deficiencies, noted above. At the very least the delay in production caused by method for activating or conditioning and also the complicated details of the procedure. Given the importance for operating Ag-based highly selective catalysts under optimum performance conditions, there is a continued need to develop new and improved methods that can be used for start-up of a process for the epoxidation of olefins, especially ethylene.

SUMMARY OF THE INVENTION

The present invention relates to a process for the preparation of a catalyst useful for the vapor phase production of ethylene oxide from ethylene and oxygen comprising the steps of providing a catalyst precursor comprising an inert support having a catalytically effective amount of a silver containing compound, a promoting amount of an alkali metal containing compound, and a promoting amount of a transition metal containing compound disposed thereon; calcining the catalyst precursor to convert the silver in the silver containing compound to metallic silver by heating the catalyst precursor to form a catalyst; and curing the catalyst in an inert gas atmosphere at temperatures of about 250° C. to about 600° C. for a period of about 1 hour to 200 hours.

DETAILED DESCRIPTION OF THE INVENTION

The present invention discloses a method for producing a high selectivity catalyst that does not require conditioning at start-up to achieve optimum performance. In this method, the high selectivity catalyst has been subjected to a curing step during or after production. When the catalyst is charged in the plant, it is ready to provide its optimum performance without a delay. As mentioned above, avoiding the conditioning step, at the very least, allows a considerable saving in time and expense for the operator of the catalyst. It has also been surprisingly found that a high selectivity catalyst prepared according to the present invention has a higher selectivity than catalysts prepared according to prior art methods. Catalysts prepared according to the present invention have a selectivity that is from 0.5 to 2 percentage points higher than if the catalyst had been prepared according to prior art methods.

The present invention relates to a process for making high selectivity catalyst involving an innovative curing step. By "high selectivity catalyst" it is meant a silver-based supported catalyst which achieves a selectivity that is greater than 84% and contains at least one additional promoter, beside Cs, especially a transition element from groups VIB and VIIB of the Periodic Table of Elements. The support employed in this invention may be selected from a large number of solid, refractory supports that may be porous. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. A preferred support is comprised of alpha-alumina having a very high purity; i.e., at least 90 wt. % pure. The remaining components may include inorganic oxides other than alpha-alumina, such as aluminum silicate, silica, alkali metal oxides (e.g., sodium oxide), alkaline earth metal oxides, and trace amounts of other metal-containing or non-metal-containing additives or impurities.

The support may be made utilizing conventional techniques well known to those skilled in the art. Alternatively, the support may be purchased from a catalyst support provider.

The support is preferably porous and has a B.E.T. surface area of at most 20 $m^2/g$, preferably from 0.1 to 10 $m^2/g$, and more preferably from 0.5 to 5 $m^2/g$. As used herein, the B.E.T. surface area is deemed to have been measured by the method as described in Brunauer, Emmet and Teller in J. Am. Chem. Soc. 60 (1938) 309-316. The support may have a monomodal pore size distribution or a multi-modal pore size distribution.

Regardless of the character of the support used, it is usually shaped into particles, chunks, pieces, pellets, rings, spheres, wagon wheels, cross-partitioned hollow cylinders, and the like, of a size suitable for employment in fixed-bed epoxidation reactors. Desirably, the support particles may have equivalent diameters in the range from about 3 mm to about 12 mm and preferably in the range from about 5 mm to about 10 mm, which are usually compatible with the internal diameter of the tubular reactors in which the catalyst is placed. Equivalent diameter is the diameter of a sphere having the same external surface (i.e., neglecting surface within the pores of the particle) to volume ratio as the support particles being employed.

In order to produce a catalyst for the oxidation of ethylene to ethylene oxide, a support having the above characteristics is then provided with a catalytically effective amount of silver on its surface. The catalyst is prepared by impregnating the support with a silver compound, complex or salt dissolved in a suitable solvent. Preferably, an aqueous silver solution is used. After impregnation, the excess solution is removed from the impregnated support, and the impregnated support is heated to evaporate the solvent and to deposit the silver or silver compound on the support as is known in the art.

Preferred catalysts prepared in accordance with this invention contain up to about 45% by weight of silver, expressed as metal, based on the total weight of the catalyst including the support. The silver is deposited upon the surface and throughout the pores of a porous refractory support. Silver contents, expressed as metal, from about 1% to about 40% based on the total weight of the catalyst are preferred, while silver contents from about 8% to about 35% are more preferred. The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide. Useful silver containing compounds which are silver precursors non-exclusively include silver nitrate, silver oxide, or a silver carboxylate, e.g., silver oxalate, silver citrate, silver phthalate, silver lactate, silver propionate, silver butyrate and higher fatty acid salts and combinations thereof.

Also deposited on the support, either prior to, coincidentally with, or subsequent to the deposition of the silver is a promoting amount of a rhenium component, which may be a rhenium-containing compound or a rhenium-containing complex. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Also deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of silver, support, alkali metal promoters, rhenium component, and optional additional promoters of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. In the epoxidation process, it may be desirable to intentionally change the operating conditions to take advantage of certain catalytic properties even at the expense of other catalytic properties. The preferred operating conditions will depend upon, among other factors, feedstock costs, energy costs, by-product removal costs and the like.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 10 parts per million to about 1000 parts per million, preferably from about 20 parts per million to about 500 parts per million, and more preferably from about 30 parts per million to about 350 parts per million of total catalyst expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include a diamino alkane having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially non-polar. In general, the solvent should have sufficient solvating power to solubilize the solution components. At the same time, it is preferred that the solvent be chosen to avoid having an undue influence on, or interaction with, the solvated promoters.

The concentration of silver in the impregnating solution is typically in the range from about 1.0% by weight up to the maximum solubility afforded by the particular solvent/solubilizing agent combination employed. It is generally very suitable to employ solutions containing from about 5% to about 45% by weight of silver, with concentrations of from about 10 to about 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. A single impregnation or a series of impregnations, with or without intermediate drying, may be used, depending, in part, on the concentration of the silver component in the solution. Impregnation procedures are described in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, rhenium component, alkali metal component, and the optional other promoters, the impregnated support/catalyst precursor is calcined for a time sufficient to reduce the silver salt to the catalytically active silver metal and to remove substantially all the volatile components from the impregnated support to result in a catalyst. Preferably the calcination of the impregnated support occurs in an atmosphere that is an inert gas atmosphere. By "inert gas atmosphere" it is meant an atmosphere that does not react with the components of the catalyst precursor. Typical inert ambients include He, Ar, Ne, Xe, $N_2$ and mixtures thereof. Optionally, the inert gas atmosphere may comprise a mixture of an inert gas with from about 1 ppm to about 0.1% oxygen. The calcination may be accomplished by heating the impregnated support, preferably at a gradual rate, to a temperature in the range from about 200° C. to about 600° C., preferably from about 200° C. to about 500° C., and more preferably from about 250° C. to about 450° C., at a pressure in the range from 0.5 to 35 bar.

In another embodiment, the calcination occurs in air, or diluted air. Diluted air is air that had been mixed with an inert gas. The diluted air may comprise from 0.1 to 21% oxygen. In this case, a temperature in the range from about 200° C. to about 500° C. is used, preferably from about 200° C. to about 400° C., and more preferably from about 230° C. to about 350° C., at a pressure in the range from 0.5 to 35. When the calcination occurs in air, the most preferred calcination temperature is less than about 300° C.

In terms of the length of calcination, generally the higher the temperature, the shorter the required heating period. Calcination may be accomplished in any type of heating apparatus or furnace. It is preferable to use gradual, step-wise heating for calcinations. For instance the step-wise heating could be implemented by placing the catalyst precursor on a moving belt with multiple heating zones so that the catalyst precursor enters the furnace at ambient temperature and then passes through one or more zones of gradually increasing temperature until a maximum temperature is obtained. After reaching the maximum temperature the catalyst precursor is passed through one or more zones of gradually decreasing temperature until the catalyst precursor exits the furnace at approximately ambient temperatures. In an alternative embodiment continuous heating is used.

After the calcining step, the catalyst formed thereby is subjected to a curing step. In this step, the catalyst is heated under an inert gas atmosphere. The curing step takes place at a temperature of about 250° C. to about 600° C., preferably 275° C. to about 500° C., and most preferably 300 to about 450° C. for a period of about 10 minutes to about 200 hours, preferably about 1 hour to 6 hours. In one embodiment, after the calcining step, the catalyst is cooled to less than 50° C. and the curing step occurs after an interval of time. In this embodiment the curing can occur on the manufacturing site or instead off-site.

In a separate embodiment, the curing step takes place immediately after the calcining step in the same heating apparatus, without any cooling interval. For example, if the calcination is taking place on a moving belt furnace, curing is accomplished by allowing the catalyst to remain in one or more heating zones for a longer period of time than would be necessary for calcination.

After calcining the high selectivity catalyst, the catalyst is loaded into the reactor tubes of an epoxidation reactor, typically a fixed bed, tubular reactor, utilizing conventional loading methods well known to those skilled in the art. The epoxidation process may be carried out by continuously contacting an oxygen-containing gas with an olefin, preferably ethylene, in the presence of the previously-described catalyst produced by the invention. Oxygen may be supplied to the reaction in substantially pure molecular form or in a mixture such as air. By way of example, reactant feed mixtures may contain from about 0.5% to about 45% ethylene and from about 3% to about 15% oxygen, with the balance comprising comparatively inert materials including such substances as carbon dioxide, water, inert gases, other hydrocarbons, and the reaction moderators described above. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

An additional component of the feed to the reactor is a moderator. The moderator material typically includes, but is not limited to, organic chlorides such as chloromethanes, chloroethanes, chloropropanes and other chloroalkanes, as well as chloroalkenes such as vinyl chlorides, and chloropropenes. Other organic chlorides, as well as other organic halides, are not excluded. In particular, the moderator material is intended to include the effective sum of all the organic chloride (or alternatively organic halide) moieties that are in a feed gas mixture. The quantity of the organic chloride moieties that is in the feed gas mixture is generally in the range of 0.5 to 15 parts per million, by volume.

A usual method for the ethylene epoxidation process comprises the vapor-phase oxidation of ethylene with molecular oxygen, in the presence of the inventive catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, un-used reactant, and byproducts to exit the reactor chamber.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide.

The previously-described catalysts have been shown to be particularly selective for oxidation of ethylene with molecular oxygen to ethylene oxide especially at high ethylene and oxygen conversion rates. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu. ft. catalyst/hr. The feed composition at the reactor inlet may typically comprises (by volume %) 5-40% ethylene, 3-12% $O_2$; 0.3% to 20%, preferably 0.3 to 5%, more preferably 0.3 to 1% of $CO_2$; 0-3% ethane, an amount of one or more chloride moderators as described above; and the balance of the feed being comprised of argon, methane, nitrogen or mixtures thereof.

EXAMPLES

The invention will now be described in more detail with respect to the following non-limiting.

Example 1

Silver based high selectivity catalyst preparation followed generally conventional procedures, as disclosed above. Specifically, a 15 Kg portion of alumina support was placed in a vessel and evacuated to about 0.1 torr prior to impregnation. To the above silver solution were added aqueous solutions of cesium hydroxide, perrhenic acid, and ammonium sulfate in order to prepare a catalyst composition according to examples 5-10 of U.S. Pat. No. 4,766,105 to Lauritzen et al. After thorough mixing, the promoted silver solution was aspirated into the evacuated flask to cover the carrier while maintaining the pressure at about 0.1 torr. The vacuum was released after about 3 minutes to restore atmospheric pressure. Subsequently, the excess impregnation solution was drained from the impregnated carrier.

Calcination of the wet catalyst was performed on a moving belt calciner. In this unit, the wet catalyst was transported on a stainless steel belt through a multi-zone furnace. All zones of the furnace were continuously purged with pre-heated, nitrogen and the temperature was increased gradually as the catalyst passed from one zone to the next. The heat supplied to the catalyst was radiated from the furnace walls and from the preheated nitrogen. In this example, the wet catalyst entered the furnace at ambient temperature. The catalyst's temperature was increased gradually to a maximum of about 450° C. as it passed through the heated zones. In the last (cooling) zone, the temperature of the now calcined catalyst was gradually lowered to less than 100° C. before it emerged into the open air atmosphere. The total residence time in the furnace was approximately 45 minutes. The catalyst was exposed to the maximum temperature for 5 minutes.

A portion of the calcined catalyst was then cured by placing it in a tubular vessel, which was placed in an oven and heated in a current of nitrogen, at 300° C., for 12 hours. The temperature of the now cured catalyst was gradually lowered to less than 100° C. before it was exposed to the open air atmosphere.

The cured catalyst was charged into a 32.5 mm reactor tube and a nitrogen gas was allowed to flow through the catalyst bed under a pressure of about 2000 Kilopascal. The temperature of the reactor was increased gradually up to 190° C. and then the following gas mixture was allowed to flow through the reactor and replace the nitrogen in the reactor:
25% ethylene;
7% oxygen;
2% carbon dioxide;
ethyl chloride (moderator), as needed to control the catalytic performance. balance nitrogen.

The temperature of the reactor was raised in order to produce an effluent gas containing 2.5% ethylene oxide. Within 40 hours from the introduction of the gas mixture, the effluent contained the targeted 2.5% ethylene oxide and the selectivity peaked at 90.5%. The temperature of the catalyst through that period did not exceed 240° C. The performance showed that the catalyst was not in need for a discrete activation step. Such performance would not have been expected by a person of ordinary skill in the art.

In a co-pending patent application "Method for Preparing an Epoxidation Catalyst", U.S. Ser. No. 13/109,657 filed on the same date as the present application, a two-step calcination is disclosed that eliminates the need for the catalyst "initiation" or conditioning period. The treatment includes first heating the catalyst precursor in an inert atmosphere and then the calcination continues in an oxygen-containing atmosphere at a temperature from about 350° C. to about 450° C. for a time period of up to about 5 minutes.

Example 2

Comparative Example

A portion of the same catalyst that was prepared in example 1 was used without the curing step. The catalyst was tested according to the protocol that was described in example 1. The catalyst was very active and within the first 100 hours of the test the selectivity was lower than 85%.

Example 3

A portion of the same catalyst that was prepared in example 1 was cured by re-calcining the catalyst in the same moving belt calciner that was used in the first calcination in inert nitrogen. The calciner's belt was stopped when the catalyst was in the hottest zone in the furnace, at the peak temperature of 320° C. The belt's regular speed was resumed after 60 min. The catalyst was then tested using the testing procedure in example 1. Within 60 hours of the start of the test the selectivity of the catalyst peaked at 89.7%. The temperature of the catalyst through that period did not exceed 240° C. This high performance was achieved without use of a conditioning step that would normally be required for the high selectivity catalyst.

Example 4

Silver based high selectivity catalyst preparation followed the details in example 1. Then the calcination was performed on a moving belt calciner in inert nitrogen. The calciner's belt was stopped when the catalyst was in the hottest zone in the furnace, at the peak temperature of 320° C. The belt regular speed was resumed after 60 min. The produced catalyst was calcined and cured during the extended heating at the peak temperature. The catalyst was then tested using the testing procedure in example 1. Within 40 hours of the start of the test the selectivity of the catalyst peaked at 89.

Example 5

A portion of the same catalyst that was prepared in example 1 was cured by placing it in a tubular vessel, which was placed in an oven and heated in a current of Argon, at 300° C., for 6 hours. The temperature of the now cured catalyst was gradually lowered to less than 100° C. before it was exposed to the open air atmosphere. The catalyst was then tested using the testing procedure in example 1. Within 100 hours of the start of the test the selectivity of the catalyst peaked at 90.1%. The temperature of the catalyst through that period did not exceed 245° C. This high performance was achieved without the use of a conditioning step that would normally be required for the high selectivity catalyst.

Example 6

Silver based high selectivity catalyst preparation followed the details in example 1. The calcination was performed on a moving belt calciner; in this example the gas flowing inside of the furnace was air, instead of nitrogen. The catalyst's temperature was increased gradually to a maximum of about 270° C. as it passed through the heated zones. The total residence time in the furnace was approximately 30 minutes. A portion of the calcined catalyst was then cured by placing it in a tubular vessel, which was placed in an oven and heated in a current of nitrogen, at 300° C., for 6 hours. The catalyst was then tested using the procedure in example 1. Within 100 hours of the start of the test the selectivity of the catalyst peaked at 90.5%. The temperature of the catalyst through that period did not exceed 240° C. This high performance was achieved without use of a conditioning step that would normally be required for the high selectivity catalyst. Such performance would not have been expected by a person of ordinary skill in the art.

Example 7

A sample of the calcined catalyst in example 6 was tested without curing. The catalyst was not able to achieve the targeted work rate and its performance degraded fast. This example demonstrates that when a catalyst is prepared according to the prior art, without curing, the catalyst requires a conditioning step in order to perform satisfactorily. By contrast catalysts of the present invention, which are prepared by a process incorporating a curing step, do not require conditioning.

What we claim is:

1. A process for the preparation of a catalyst useful for the vapor phase production of ethylene oxide from ethylene and oxygen comprising:
    providing a catalyst precursor comprising an inert support having a catalytically effective amount of a silver containing compound, a promoting amount of an alkali metal containing compound, and a promoting amount of a transition metal containing compound disposed thereon;
    calcining the catalyst precursor in a first inert gas atmosphere and at a calcination temperature to convert the silver in the silver containing compound to catalytically active metallic silver, to remove volatile components from the inert support of said catalyst precursor, and to form a catalyst;
    cooling the catalyst to a temperature below the calcination temperature;
    curing the catalyst produced by said calcining in a second inert gas atmosphere and at a curing temperature of about 250° C. to about 600° C. for a period of about 1 hour to 200 hours to provide a cured catalyst; and
    charging said cured catalyst into reactor tubes of an epoxidation reactor.

2. The process of claim 1 wherein said first inert gas atmosphere of said calcining comprises a mixture of an inert gas and from about 1 ppm to 0.1% oxygen.

3. The process of claim 1 wherein the temperature of the calcining step is from about 300° C. to about 500° C.

4. The process of claim 1 wherein the temperature of the curing step is about 300° C. to about 450° C.

5. The process of claim 1 wherein the period of the curing step is about 2 hours to 6 hours.

6. The process of claim 1 wherein said cooling the catalyst is to a temperature of less than about 50° C.

7. The process of claim 1 wherein the transition metal comprises rhenium.

8. The process of claim 1 wherein the alkali metal containing compound comprises cesium.

9. The process of claim 1 further comprising exposing said cured catalyst to air prior to charging said cured catalyst into said reactor tubes of said epoxidation reactor.

* * * * *